(12) United States Patent
Nikodem

(10) Patent No.: US 7,335,021 B2
(45) Date of Patent: Feb. 26, 2008

(54) METHODS AND APPARATUS TO FACILITATE ORTHODONTIC ALIGNMENT OF TEETH

(76) Inventor: Stephen Gerard Nikodem, 134 Frontenac Forest, St. Louis, MO (US) 63131

(*) Notice: Subject to any disclaimer, the term of this patent is extended or adjusted under 35 U.S.C. 154(b) by 0 days.

(21) Appl. No.: 10/767,671

(22) Filed: Jan. 29, 2004

(65) Prior Publication Data
US 2005/0064359 A1  Mar. 24, 2005

Related U.S. Application Data

(60) Provisional application No. 60/504,896, filed on Sep. 22, 2003.

(51) Int. Cl.
*A61C 7/00* (2006.01)
(52) U.S. Cl. .................................................. 433/18
(58) Field of Classification Search ................ 433/18, 433/21, 24, 7, 20
See application file for complete search history.

(56) References Cited

U.S. PATENT DOCUMENTS

| 3,127,677 | A | * | 4/1964 | Schachter | 433/17 |
| 3,835,538 | A | * | 9/1974 | Northcutt | 433/9 |
| 4,187,610 | A | * | 2/1980 | Ziegler | 433/24 |
| 4,256,456 | A | * | 3/1981 | Wallshein | 433/21 |
| 5,112,221 | A | * | 5/1992 | Terry | 433/21 |
| 5,246,366 | A | * | 9/1993 | Tracey | 433/21 |
| 5,312,247 | A | * | 5/1994 | Sachdeva et al. | 433/7 |

* cited by examiner

Primary Examiner—Melba Bumgarner
(74) Attorney, Agent, or Firm—Armstrong Teasdale LLP

(57) ABSTRACT

An apparatus facilitates treatment of a tooth that is at least partially impacted. The apparatus includes a wire including a first end, a second end, and a substantially planar body extending therebetween. The first end is configured to couple to a tooth. The second end is configured to secure the apparatus relative to the tooth such that the wire applies a substantially continuous force to the tooth.

12 Claims, 3 Drawing Sheets

METHODS AND APPARATUS TO FACILITATE ORTHODONTIC ALIGNMENT OF TEETH

CROSS REFERENCE TO RELATED APPLICATION

This application claims the benefit of U.S. Provisional Application No. 60/504,896, filed Aug. 22, 2003.

BACKGROUND OF THE INVENTION

This invention relates generally to impacted teeth, and more specifically to methods and apparatus to facilitate repositioning teeth.

Orthodontia generally involves the treatment of malocclusions by the use of fixed appliances, such as brackets and archwires. A plurality of standardized orthodontic appliances are available for use by an orthodontist to facilitate straightening teeth. However, when a malocclusion involves one or more impacted teeth, especially the maxillary canines, the repositioning of such teeth may require the cooperation of several dental specialties, particularly oral surgery and orthodontics.

To facilitate repositioning impacted teeth, at least some known ligation techniques require surgically exposing the impacted tooth and attaching a first end of a chain or a wire around a neck of the impacted tooth. The second end of the chain is then coupled to an anchoring means such that a force is applied to the impacted tooth. Moreover, at least some known ligation techniques also require the wire to be braided between the impacted tooth and the second end. Over time, as the tooth is repositioned in response to the force, the pressure applied from the chain to the tooth lessens, and the chain must be re-tightened to the anchoring means to ensure an adequate thrusting force is applied to the tooth. In addition, as the tooth is shifted, a portion of the tooth structure surrounding the impacted tooth may be damaged as the chain links press against the structure. Furthermore, occasionally an additional surgical procedure may be necessary to re-tightened the chain around the tooth.

To facilitate reducing an amount of tooth structure damage, at least some other known ligation techniques bond an orthodontic fixture to an external surface of the tooth. An orthodontic gold chain is then coupled to the fixture and coupled to an anchoring means such that a considerable force is applied to the tooth. However, as the tooth shifts, the pressure applied to the tooth may lessen, such that the gold chain must be continuously re-tightened to ensure an adequate thrusting pressure is again applied to the impacted tooth. As a result, only an intermittent interruptive thrusting force is applied to the impacted tooth.

BRIEF SUMMARY OF THE INVENTION

In one aspect, an apparatus for repositioning a tooth that is at least partially impacted is provided. The apparatus includes a wire including a first end, a second end, and a substantially planar body extending therebetween. The first end is configured to couple to a tooth, and the second end is configured to secure the apparatus relative to the tooth such that the wire applies a substantially continuous force to the tooth.

In a further aspect, a method for treating a tooth that is at least partially impacted is provided. The method comprises coupling a first end of a wire to an impacted tooth, the wire having a substantially planar body extending between the first end and a second end, and coupling the wire second end to an anchoring device such that the wire applies a substantially continuous force to the impacted tooth.

DETAILED DESCRIPTION OF THE INVENTION

As used herein, the term "wire" may include any substantially planar device or apparatus which functions as described herein to facilitate repositioning an impacted tooth. The above examples are intended as exemplary only, and thus are not intended to limit in any way the definition and/or meaning of the terms "apparatus" or "wire." In addition, although the methods and apparatuses described herein are described in association with a maxillary canine tooth, it should be understood that the methods and apparatuses described herein may be applicable to any tooth that is at least partially impacted, and to any non-impacted tooth requiring eruption and/or desired repositioning. Additionally, it should also be noted that the methods and apparatuses described herein may also be used with multiple teeth. Accordingly, practice of the present invention is not limited to methods and apparatus for repositioning or treatment of maxillary canine teeth.

Figure 1:
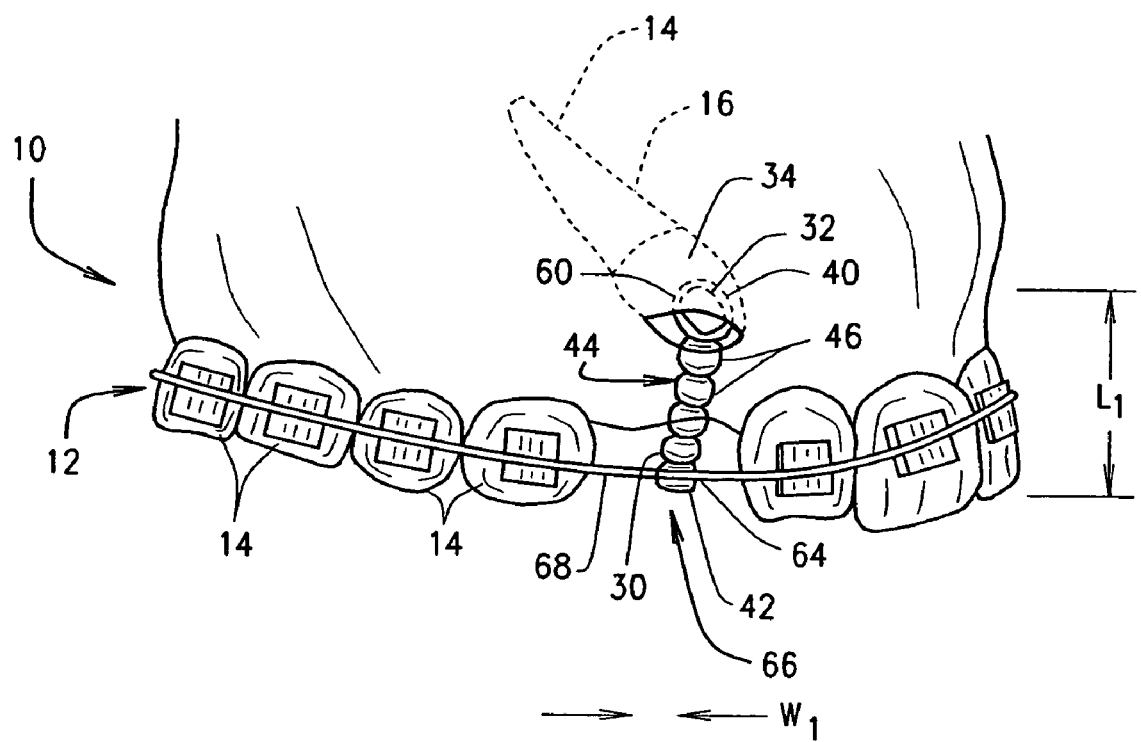
FIG. 1 is an front elevational view of an exemplary apparatus coupled to an upper row of teeth to facilitate treatment of an impacted tooth.
Figure 2:
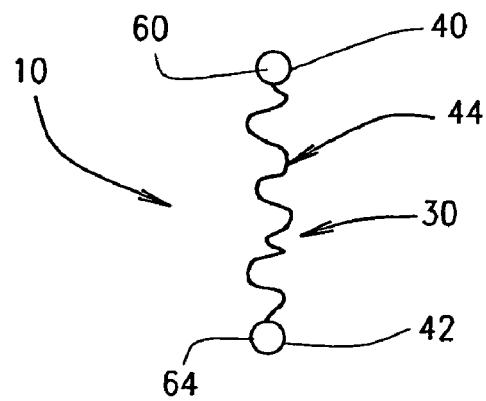
FIG. 2 is an enlarged view of an exemplary alternative embodiment of a guide wire that may be used with the apparatus shown in FIG. 1.
Figure 3:
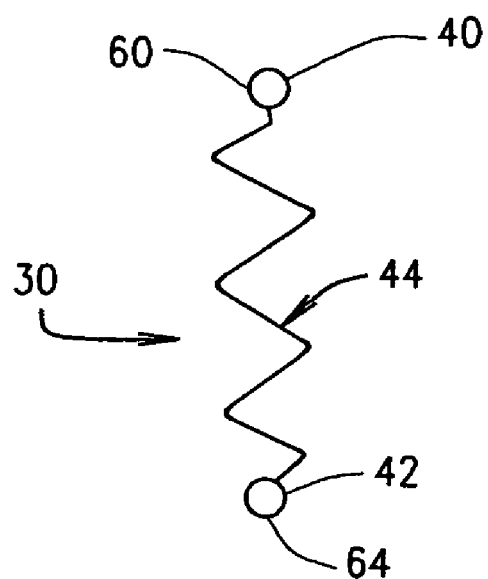
FIG. 3 is an enlarged view of another exemplary alternative embodiment of a guide wire that may be used with the apparatus shown in FIG. 1.
Figure 4:
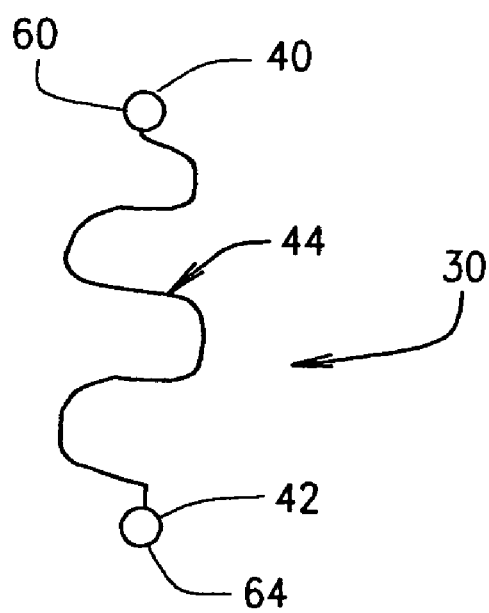
FIG. 4 is an enlarged view of a further exemplary embodiment of a guide wire that may be used with the apparatus shown in FIG. 1.
Figure 5:
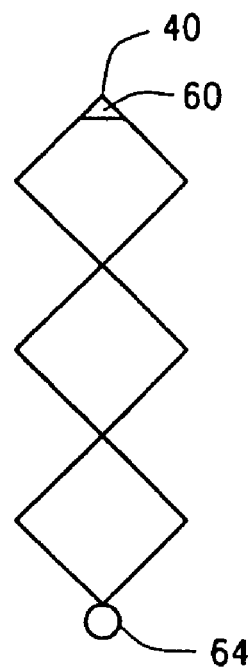
FIG. 5 is an enlarged view of an additional exemplary embodiment of a guide wire that may be used with the apparatus shown in FIG. 1.
Figure 6:
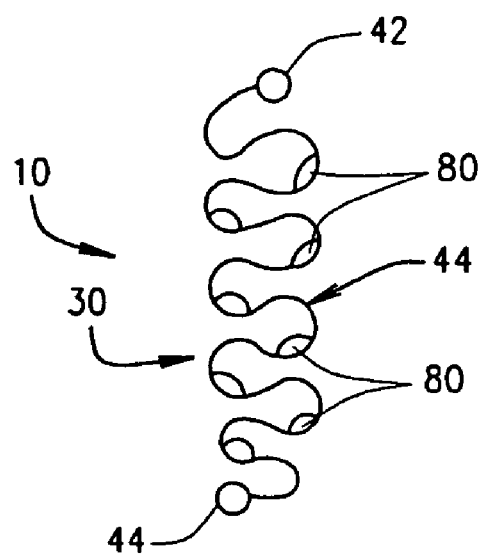
FIG. 6 is an enlarged view of another exemplary embodiment of a guide wire that may be used with the apparatus shown in FIG. 1.

FIG. 1 is an front elevational exemplary view of an apparatus 10 coupled to an upper row 12 of teeth 14 to facilitate treatment of an impacted tooth 16. In an alternative embodiment, apparatus 10 is used to facilitate orthodontic repositioning and/or treatment of any tooth 14, including non-impacted teeth. FIG. 2 is an enlarged view of an alternative exemplary embodiment of a guide wire 30 that may be used with apparatus 10. FIG. 3 is an enlarged view of another exemplary alternative embodiment of a guide wire 30 that may be used with apparatus 10. FIG. 4 is an enlarged view of a further exemplary embodiment of a guide wire 30 that may be used with apparatus 10. FIG. 5 is an enlarged view of a further exemplary embodiment of a guide wire 30 that may be used with apparatus 10. FIG. 6 illustrates another exemplary embodiment of a guide wire that may be used with apparatus 10. In the exemplary embodiment, apparatus 10 includes a guide wire member 30 and an orthodontic fixture or bracket 32. In one embodiment, guide wire 30 is a spring. Fixture 32 is known in the art and is coupled to an external surface 34 of impacted tooth 16.

Guide wire 30 includes a first end 40, a second end 42, and a body 44 extending therebetween. In the exemplary embodiment illustrated in FIG. 1, body 44 includes a plurality of eyelets 46 extending between ends 40 and 42. In the exemplary embodiment, eyelets 46 are each sized substantially similar. In an alternative embodiment, at least one eyelet 46 is sized differently than the remaining eyelets 46. The number and size of eyelets 46 is variably selected depending on the intended application of apparatus 10.

Guide wire 30 is not limited to including eyelets 46, but rather guide wire body 44 may be any substantially planar shape that enables apparatus 10 to perform as described herein. For example, in the exemplary embodiment shown in FIG. 2, body 44 is substantially serpentine shaped, in the exemplary embodiment shown in FIG. 3, body 44 is substantially sinusoidal shaped, and in the exemplary embodiment shown in FIG. 4, body 44 is substantially zigzagged shaped. In other embodiments, body 10 extends substantially non-linearly between ends 40 and 42.

Guide wire 30 is substantially planar between ends 40 and 42 in each embodiment. Accordingly, in each embodiment, body 44 is not braided. Additionally, in the exemplary embodiment, body 44 does not overlap other portions of guide wire 30. In the exemplary embodiment, body 44 is formed integrally with ends 40 and 42, such that ends 40 and 42 are each substantially co-planar with body 44. In an alternative embodiment, either of end 40 and/or 42 is coupled to body 44. In a further alternative embodiment, body 44 is fabricated from a plurality of members coupled together. In a another embodiment, ends 40 and 42 are not substantially planar with wire body 44 and rather at least one end 40 and/or 42 includes a portion that overlaps itself, thus forming a lumen or a loop, for example. In another alternative embodiment, body 44 is substantially planar and at least one end 40 and/or 42, and/or body 44 includes a fastening mechanism, such as a hook or clamp (not shown) which may be utilized to facilitate activation or stretching of wire 30. In other embodiments, ends 40 and/or 42 are crimpable to enable ends 40 and 42 to be affixed once wire 30 has been activated.

Body 44 has a thickness measured between opposite sides of body 44. The body thickness is variably selected depending on the intended application of apparatus 10. In the exemplary embodiment, the body thickness is substantially constant through guide wire 30. In an alternative embodiment, an inner surface of guide wire 30 is substantially flat while the body thickness varies across wire 30. In addition, body 44 has a width $W_1$ and a length $L_1$ measured between ends 40 and 42. Body width $W_1$ and length $L_1$ are also variably selected depending on the intended use of apparatus 10.

In each embodiment, body first end 40 includes a fastener means 60 that enables apparatus 10 to be secured to impacted tooth 16. In the exemplary embodiment, fastener means 60 is an eyelet that is sized to securely couple to orthodontic fixture 32. Body second end 42 includes a second fastener means 64 that facilitates securely fastening apparatus 10 to an anchoring means 66. In the exemplary embodiment, anchoring means 66 includes a known arch wire 68. Alternatively, anchoring means 66 include, but are not limited to, an adjacent tooth 14, a ligature wire (not shown), and/or an arch wire 68.

In the exemplary embodiment, body 44 and ends 40 and 42 are each fabricated from the same material. In an alternative embodiment, either end 40 and/or end 42 is fabricated from a different material than body 44. In each embodiment, ends 40 and 42, and body 44 are fabricated from a material that enables guide wire 30 to apply a thrusting or eruptive force to impacted tooth 16, as described herein. In one embodiment, wire 30 is fabricated with a material that is superelastic and that enables substantially pure elastic deformability of guide wire 30, such as, but not limited, to Nitinol® or any of several known shaped memory alloys (SMA) that has properties that develop a shaped memory effect (SME). For example, in one embodiment, wire 30 is fabricated from, but is not limited to being fabricated from a thermally treated metal alloy (TMA) such as, nickel titanium, beta titanium, copper nickel titanium, or any combination thereof. In one embodiment, wire 30 contracts when heated.

During use, initially a portion of impacted tooth 16 is exposed using a known surgical procedure, and orthodontic fixture 32 is bonded to tooth surface 34. Apparatus 10 is then coupled to tooth 16 such that wire first end 40 is secured to fixture 32. Guide wire 30 is then stretched into position such that second end 42 may be secured to anchoring means 66 to apply a force to tooth 16. As guide wire 30 is stretched, wire 30 is deformed to an activated position. More specifically, a relative location of anchoring means 66 is selected to facilitate applying a force to tooth 16 that causes tooth 16 to erupt into a desired location relative to other teeth 14.

The combination of the substantially flat profile shape of guide wire 30 and the material used in fabricating guide wire 30, facilitates a substantially constant force being applied to impacted tooth 16 when wire 30 is activated. More specifically, the force applied by guide wire 30 facilitates tooth 16 being repositioned along the path of least resistance into the desired positioned. In addition, the combination of the flat profile and the material of guide wire 30 facilitates apparatus 10 applying a force to impacted tooth 16 for a longer time period than at least other known conventional orthodontic chains used to reposition impacted teeth. Therefore, second end 42 is facilitated to be re-tightened less frequently than may be possible using at least some known conventional orthodontic gold chains. Moreover, because guide wire 30 does not include braided links, and because wire 30 does not require as much force as known orthodontic gold chains to reposition an impacted tooth 16, during repositioning, apparatus 10 facilitates causing less damage and periodontum to surrounding tooth structure. In addition, because apparatus 10 applies a substantially constant force to teeth 14, apparatus 10 also facilitates repositioning teeth 14 in a more timely fashion than other known orthodontic ligation devices.

Accordingly, wire 30 may be used to correct a patient's occlusion or bite, as well as other dental/orthodontic/oral surgery procedures, including, but not limited to bite correction. More specifically, by attaching apparatus 10 from one arch, such as the patient's upper teeth, to the other arch, such as the patient's lower teeth, the continuous force applied by apparatus 10 can be utilized to facilitate aligning the patients jaw efficiently and expeditiously.

In the exemplary embodiment illustrated in FIG. 6, body 44 includes a plurality of loops or coupling mechanisms 80 which may be selectively used to stretch wire 30 to facilitate activation of wire 30. In alternative embodiments, body 44 and/or ends 40 or 42 includes a plurality of coupling mechanisms 80 which may be selectively used to stretch wire 30 to facilitate activation of wire 30. In other embodiments, ends 40 and/or 42 are crimpable to enable ends 40 and 42 to be affixed once wire 30 has been activated. Guide wire 30 is not limited to only including loops 80, and may include different coupling mechanisms at different locations along wire 30. Moreover, wire coupling mechanisms 80 are not limited to being only loops 80, but rather guide wire 30 may include other coupling mechanisms, such as, but not limited to, hooks, clamps, ornaments, or clips.

The above-described impacted tooth apparatus is highly reliable. The apparatus includes a wire that is coupled to a fixture coupled to the external surface of an impacted tooth. The combination of the substantially flat profile of the apparatus, and the material used in fabricating the apparatus, facilitates applying a substantially continuous and uniform force to the impacted tooth. Accordingly, eruption times of impacted teeth are facilitated to be reduced, as the apparatus does not need to be re-tightened as frequently as other known orthodontic chains.

Exemplary embodiments of apparatuses used to reposition impacted teeth are described above in detail. The apparatuses are not limited to the specific embodiments described herein, but rather, components of each apparatus may be utilized independently and separately from other components described herein. For example, each apparatus component can also be used in combination with other impacted tooth repositioning apparatuses.

While the invention has been described in terms of various specific embodiments, those skilled in the art will recognize that the invention can be practiced with modification within the spirit and scope of the claims.

What is claimed is:

1. An apparatus for facilitating treatment of a tooth that is at least partially impacted, said apparatus comprising a wire fabricated at least partially from a superelastic material, said wire comprising a first end, a second end, and a substantially planar body extending therebetween, said body having a substantially uniform thickness and movable between a static position and an activated position, said body comprising at least one eyelet formed between said first end and said second end, wherein said body is stretched between said first end and said second end, said first end comprising a first fastener configured to couple to an orthodontic fixture coupled to an outer surface of a tooth that is at least partially impacted, with said body stretched to the activated position said second end comprising a second fastener configured to couple to an anchoring device and secure said apparatus relative to the tooth, such that said wire applies a substantially constant force to the tooth as said body moves from the activated position to the static position to urge said first end toward said second end to erupt the at least partially impacted tooth.

2. An apparatus in accordance with claim 1 wherein said body is at least one of zigzagged shaped, serpentine shaped, and sinusoidal shaped.

3. An apparatus in accordance with claim 1 wherein said first end is configured to couple to the tooth without circumscribing the tooth.

4. An apparatus in accordance with claim 1 wherein said body comprises a spring extending between said first and second ends.

5. An apparatus in accordance with claim 1 wherein said wire is fabricated at least partially from a shaped memory alloy (SMA).

6. A method for treating a tooth that is at least partially impacted, said method comprising:

coupling a first end of a wire comprising a first fastener to an orthodontic fixture coupled to an outer surface of an at least partially impacted tooth, the wire fabricated at least partially from a superelastic material and having a substantially planar body extending between the first end and a second end, wherein the body has a substantially uniform thickness and is movable between a static position and an activated position, wherein the body is stretched between the first end and the second end;

stretching the body from the static position to the activated position; and coupling the wire second end comprising a second fastener to an anchoring device with the body stretched to the activated position such that the wire applies a substantially constant force to the at least partially impacted tooth as the body moves from the activated position to the static position to urge the first end toward the second end to erupt the at least partially impacted tooth.

7. A method in accordance with claim 6 wherein coupling the wire second end to an anchoring device further comprises coupling the wire second end to the anchoring device such that at least one eyelet is defined between the first and second ends of the wire.

8. A method in accordance with claim 6 wherein coupling the wire second end to an anchoring-device further comprises coupling the wire second end to the anchoring device such that the body is unbraided between the first and second ends.

9. A method in accordance with claim 6 wherein coupling a first end of a wire having a substantially planar body extending between the first end and a second end to an impacted tooth further comprises coupling the first end of the wire fabricated from a superelastic material to the impacted tooth.

10. A method in accordance with claim 6 wherein coupling a first end of a wire having a substantially planar body extending between the first end and a second end to an impacted tooth further comprises coupling the first end of the wire fabricated from a super memory alloy to the impacted tooth.

11. A method in accordance with claim 6 wherein coupling the wire second end to an anchoring device further comprises coupling the wire second end to the anchoring device such that a substantially constant spring force is applied to the impacted tooth.

12. A method in accordance with claim 6 wherein coupling the wire second end to an anchoring device further comprises coupling the wire second end to the anchoring device such that the thickness of the apparatus remains substantially uniform between the first and second ends.

* * * * *